US011449833B2

(12) United States Patent
Martin et al.

(10) Patent No.: US 11,449,833 B2
(45) Date of Patent: *Sep. 20, 2022

(54) DEVICE AND METHOD FOR DELIVERING MEDICAL LAB REPORTS

(71) Applicant: Xerox Corporation, Norwalk, CT (US)

(72) Inventors: Nathaniel G. Martin, Rochester, NY (US); Steven J. Harrington, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 199 days.

This patent is subject to a terminal disclaimer.

(21) Appl. No.: 16/877,550

(22) Filed: May 19, 2020

(65) Prior Publication Data

US 2020/0279344 A1    Sep. 3, 2020

Related U.S. Application Data

(63) Continuation of application No. 12/132,227, filed on Jun. 3, 2008, now Pat. No. 10,679,308.

(51) Int. Cl.
*G06Q 10/10* (2012.01)
*G16H 10/20* (2018.01)
*G16H 10/40* (2018.01)

(52) U.S. Cl.
CPC ............ *G06Q 10/10* (2013.01); *G16H 10/20* (2018.01); *G16H 10/40* (2018.01)

(58) Field of Classification Search
CPC .... G01S 5/0036; G01S 5/0231; G01S 5/0236; G01S 19/16; G01S 2205/05; G01S 5/02;

(Continued)

(56) References Cited

U.S. PATENT DOCUMENTS 6,192,320 B1    2/2001    Margrey et al.
7,344,079 B2    3/2008    Steusloff et al.
(Continued)

FOREIGN PATENT DOCUMENTS

JP    2005050279 A  *  2/2005

OTHER PUBLICATIONS

Marconi, M, A.F. Langeberg, G.Sirchia, and S.G. Sandler. "Improving Transfusion Safety by Electronic Identification of Patients, Blood Samples, and Blood Units." Immunohematology, vol. 16, No. 2, 2000. pp. 82-85 (Year: 2000).*

(Continued)

*Primary Examiner* — Linh Giang Le
(74) *Attorney, Agent, or Firm* — Gibb IP Law Firm, LLC (57) ABSTRACT

A system and method scan a document printed by a first document processing device (using a second document processing device separate from the first document processing device). The document has printed thereon machine readable markings that comprise information of a patient, information of at least one lab test to be performed, and formatting information for the return of the lab test results. The second document processing device identifies the lab test to be performed on the patient based on the machine readable markings. After the lab tests have been performed on the patient, the second document processing device prepares the lab test results by formatting them. These formatted lab test results are then output from the second document processing device to the first document processing device.

20 Claims, 3 Drawing Sheets

(58) Field of Classification Search
CPC ... H04W 64/003; H04B 17/27; H04B 17/318; H04B 17/382
See application file for complete search history.

(56) References Cited

U.S. PATENT DOCUMENTS

| | | | |
|---|---|---|---|
| 2001/0051879 | A1 | 12/2001 | Johnson et al. |
| 2004/0153338 | A1 | 8/2004 | Kim et al. |
| 2004/0172301 | A1 | 9/2004 | Mihai et al. |
| 2004/0176667 | A1 | 9/2004 | Mihai et al. |
| 2004/0243444 | A1* | 12/2004 | Steusloff ............... G16H 20/10 235/375 |
| 2006/0265249 | A1 | 11/2006 | Follis et al. |
| 2007/0138253 | A1 | 6/2007 | Libin et al. |
| 2007/0288268 | A1 | 12/2007 | Weeks |

OTHER PUBLICATIONS

U.S. Appl. No. 12/132,227, Office Action Communication dated Jan. 21, 2011, pp. 1-6.
U.S. Appl. No. 12/132,227, Office Action Communication dated Jul. 8, 2011, pp. 1-7.
U.S. Appl. No. 12/132,227, Advisory Action dated Sep. 21, 2011, pp. 1-3.
U.S. Appl. No. 12/132,227, Office Action Communication dated Jan. 23, 2012, pp. 1-9.
U.S. Appl. No. 12/132,227, Office Action Communication dated Jul. 11, 2012, pp. 1-11.
U.S. Appl. No. 12/132,227, Advisory Action dated Oct. 19, 2012, pp. 1-3.
U.S. Appl. No. 12/132,227, Board's Decision dated Mar. 25, 2016, pp. 1-11.
U.S. Appl. No. 12/132,227, Office Action Communication dated Jul. 13, 2016, pp. 1-10.
U.S. Appl. No. 12/132,227, Office Action Communication dated Dec. 28, 2016, pp. 1-11.
U.S. Appl. No. 12/132,227, Examiner's Answer dated Sep. 12, 2017, pp. 1-9.
U.S. Appl. No. 12/132,227, Board's Decision dated Dec. 9, 2019, pp. 1-10.
U.S. U.S. Appl. No. 12/132,227, Notice of Allowance dated Feb. 12, 2020, pp. 1-9.
U.S. Appl. No. 12/132,227, Examiner's Answer dated Mar. 13, 2013, pp. 1-13.

* cited by examiner

DEVICE AND METHOD FOR DELIVERING MEDICAL LAB REPORTS

CROSS-REFERENCE TO RELATED APPLICATIONS

The present invention claims the benefit under 35 U.S.C. § 120 as a continuation of presently pending U.S. patent application Ser. No. 12/132,227 filed on Jun. 3, 2008, now issued as U.S. Pat. No. 10,679,308 on Jun. 9, 2020, the entire teachings of which are incorporated herein by reference.

BACKGROUND AND SUMMARY

Embodiments herein generally relate to method and apparatus embodiments that use communications between document processing devices to automatically provide results of lab tests in a format that is the most appropriate for the office that prescribed the lab tests.

Medical patients are commonly referred for medical tests to a lab by giving the patient a piece of paper (a lab prescription) that describes the tests to be done. At the lab, the patient gives the lab technicians the paper and the lab technicians perform the requested test. Most of the test equipment produces electronic records, but, if the doctor's office is not capable of receiving the electronic data, it must be faxed from the lab to the doctor's office. On the other hand, if the data is returned electronically, it may be difficult to read and review with the patient. This disclosure presents a method and system whereby the results of the lab tests can be delivered to the recipient doctor's office in a form that can be accepted by the doctor's equipment and needs. In addition, the system and methods automatically read and prepare the tests based on the paper carried by the patient. The paper can also include information about the best way to return to test results to the doctor's equipment.

More specifically, the embodiments herein comprise one or more document processing devices, such as a multi-function printer (MFP) or multi-function device (MFD), that reads a request for lab tests and the results from the lab equipment and prepares a report to be transmitted back to the doctor's office. The MFP's controller processes the request and determines the appropriate method by which to reply to the request. The reply will be made either over a public or private (local or wide area) network (e.g., the internet) or by fax depending on the equipment at the recipient doctor's office.

Thus, with embodiments herein, the lab test results will be sent in the form most appropriate to the doctor's office. The appropriate form for submitting the lab results may be determined 1) by entering information at the MFP, 2) by retrieving information from a database either on the MFP or connected to the MFP, or 3) by reading the information from the form. The equipment disclosed herein can include MPFs that are capable of encoding machine readable data (such as glyphs) on the form that may be read by the lab. Such MFPs are able to encode information on the form that indicates the type of tests required so that when the form is scanned at the lab, the lab equipment can be automatically set up for the tests. The apparatus embodiments herein are also able to receive binary data encoded in a fax and process the binary information.

One specific method embodiment herein begins by scanning a document printed by a first document processing device (using a second document processing device separate from the first document processing device). The document has printed thereon machine readable markings (which can only be read by a machine and are not human-readable) as well as any necessary human readable markings (text and graphics). The machine readable markings contain information of a patient, information of at least one lab test to be performed, and formatting information for the return of the lab test results. With embodiments herein, the second document processing device identifies the lab test to be performed on the patient based on the machine readable markings.

Some embodiments herein can use the second document processing device to output to a lab technician the identification of the patient and the identification of the lab test to be performed. For example, a paper based user interface may have, for an identifier, the patient demographic data, and an indication of the preferred format for the data to be returned in machine readable format. This interface would have check boxed for the doctor to indicate the labs requested. A lab technician performs the appropriate lab tests on the patient using various lab testing equipment, that is operatively connected to, or is in communication with the second document processing device. U.S. Pat. No. 6,192, 320 "Integrative Remote Sample Analysis System" teaches how such a lab can be arranged to deliver electronic lab results to a central server and the full disclosure of this patent is incorporated herein by reference. Such a system could output this electronic data to the second document device for appropriate delivery back to the first document device. After these lab tests have been performed on the patient, the second document processing device formats the lab test results to be compatible with the needs of the first document processing device based on the formatting information that is contained within the machine readable markings.

These formatted lab test results are then output from the second document processing device to the first document processing device. These can be output by transmitting the lab test results as a facsimile transmission from the second document processing device to the first document processing device. Alternatively, a second document processing device can output lab test results directly into an electronic medical record (EMR) possibly with the intervention of the first document device. The first device processes the incoming data stream to transform the lab results into a format appropriate to the EMR. For example, the second document processing device may return a fax that is interpreted by the first document processing device as electronic data to be inserted into the EMR. In such a situation, before the document is printed, the method can identify the patient using the EMR system and select the lab test to be performed using the EMR system.

A number of devices embodiments are presented in this disclosure. One of the standalone devices presented herein comprises a document processing device that has a processor that executes instructions stored on connected computer-readable storage media to perform the various operations mentioned herein. Further, this device includes a user interface that can receive information from the patient or a medical provider, a printing engine (operatively connected to the processor) that can print the document, and a scanner (operatively connected to the processor) that scans the document. The processor processes the scanned image to identify the lab test to be performed on the patient, based on the machine readable markings.

This device further includes a communications port or ports that are operatively connected to the processor. The communications port is also operatively connected to the lab testing equipment that is used to perform the lab test on the patient and can receive the lab test results from such lab testing equipment. For example, MFP's are typically set up with two communications ports: an internet port to deliver printable files and a phone port to send and receive faxes. Either of these ports could be used to deliver the lab results depending on the requirements of the office receiving them. The processor formats the lab test results based on the formatting information from the machine readable markings, and the communications port outputs the formatted lab test results. Once again, the communications port can output the lab test results as a facsimile or as data that may be entered into an electronic medical record (EMR).

System embodiments are also disclosed herein. One system embodiment includes a first document processing device and a second document processing device that is in communication with the first document processing device. Each of these devices includes, respectively, first and second processors operatively connected to first and second computer-readable storage media. Again, the processors execute instructions stored on the first and second computer-readable storage media. Such devices also include, respectively, first and second printing engines, first and second scanners, and first and second communication ports, and first and second user interfaces (each of which is operatively connected to their respective processors).

In the description of this exemplary system embodiment, the "first" document processing device will be located at the medical provider's office that issues the lab test prescription, and the "second" document processing device will be located at the lab testing facility. The first document processing device and the second document processing device can be identical devices or different devices that can communicate with one another. Thus, the first printing engine prints the machine readable markings that contain information of the patient, information of the lab test(s) to be performed, and formatting information.

The patient then generally carries the printed document to the lab testing facility and presents the printed document to a lab technician, who then scans the document using the second document processing device. Thus, the second scanner produces a scanned image and the second processor processes the scanned image to identify the lab test to be performed on the patient based on the machine readable markings. The second document processing device can then print or display, for the lab technician, an identification of the patient and an identification of the lab test to be performed (using the second printing engine or the second user interface).

One feature of the embodiments herein is that the second communications port is operatively connected to the lab testing equipment used to perform the lab tests on the patient and therefore electronically receives the lab test results from the lab testing equipment. Another feature of the embodiments herein is that the second processor formats the lab test results based on the formatting information from the machine readable markings to convert the lab test results into a format that can be used by the first document processing device.

Then, after the lab test results are properly formatted for the first document processing device, the second communications port outputs the formatted lab test results to the first communications port. Once again, the communications port can output the lab test results as a facsimile or electronic data prepared for inclusion in a medical record. The first device then can output the data to an EMR system operatively connected to the first document processing device. In such a situation, if the lab report needs to be printed, the method can identify the patient using the EMR system and select the lab test to be printed using the EMR system.

These and other features are described in, or are apparent from, the following detailed description.

BRIEF DESCRIPTION OF THE DRAWINGS

Various exemplary embodiments of the systems and methods are described in detail below, with reference to the attached drawing figures, in which.

DETAILED DESCRIPTION

Doctor's offices (the requesting office) routinely request lab tests from labs. The results of these tests are then commonly delivered to the same and/or a different doctor's office (the receiving office) by mail, courier, e-mail, or facsimile. The requesting office typically gives the patient a printed lab test prescription form that indicates the tests that are to be performed. The patient then takes the lab test prescription form to the lab. Samples may be taken and the lab test performed using the samples. These tests are often performed on equipment that is capable of delivering result electronically. The results from the test equipment are delivered to the receiving office either electronically or through fax. The delivery method depends on the capabilities of the equipment at the receiving office.

In summary, the workflow for such lab reports is as follows. The requesting office creates a lab test prescription form designating tests to be performed on a patient, the patient takes the lab test prescription form to the lab, the lab reads the lab test prescription form, and then takes samples and performs tests, as specified on the lab test prescription form. Results of the test are then read from the machine (often electronically, occasionally manually) and the results of the test are formatted in electronic form. These results are returned to the receiving office either electronically or by fax. The receiving office receives the data, and a healthcare professional reviews the data and discusses options with the patient.

One idea herein is to deliver the lab test results to the receiving office in a format that is best for the receiving office. This involves processing the paper lab test prescription form the patient brings in from the requesting office, collecting the data from the machines that perform the tests, and delivering the data back to the receiving office in the best format.

This disclosure describes various devices and methods. The first discussion is focused on the creation of the lab test prescription form by the requesting office; the second is focused on delivering the information to the lab; and the third is focused returning the results of the lab tests to the receiving office.

With respect to the creation of the lab test prescription form, a first device resides at the requesting doctor's office. This device produces a lab test prescription form that contains machine readable and human readable information describing the tests that are to be performed and information about the patient on whom these tests are to be performed. For example, this device comprises an MFD whose controller orchestrates the following process. Patient identifiers and the tests to be performed are entered into the MFD. This information may be entered in several ways. For example, the patient ID could be entered at the device user interface and the tests entered by a paper user interface (UI) form; the patient ID, and the requested tests could be entered into the user interface on the MFP; the patient ID, and the requested tests could be entered into a browser that is running a web application running on the MFD; the patient ID; and the requested tests could be entered in an application that is monitored by the MFD; the patient ID, and the requested tests could be entered using a paper UI, etc. A paper UI is a system that uses glyphs to indicate the meaning of marks on a paper form.

The MFD then automatically obtains any additional information needed to complete the lab test prescription form. The needed information may be collected in many different ways. For example, a person may enter the data either through the device UI or through a Web UI, the device may retrieve the data from a database maintained locally on the device, and/or the device may contact a remote database, supply credentials, and retrieve the data.

After this, the MFD can create an image that encodes the relevant information on the test lab test prescription form. Such an image could be, for example, a bar code, a glyph, etc. The MFD combines the information into a single image so that the machine readable information and the human readable information are available on the same lab test prescription form. The MFD prints the resulting image on a piece of paper.

Alternative embodiments do not need to encode all of the information in machine readable form on the piece of paper. Instead, such embodiments can make the data available to the receiving site by electronic transfer. Such embodiments then just encode a reference identifier on the piece of paper so that when the patient arrives at the testing lab with the paper, this reference identifier is electronically captured, and the laboratory can then retrieve the desired information in electronic form.

A second similar or identical device resides at the lab. This second device automatically collects information on the tests to be performed, the patient on whom the tests are to be performed, and the formatting required by the receiving office. The second device arranges this information in a format that makes it most convenient to perform the tests. For example, the second device may automatically set up parameters on test devices through the lab's network. The second device may also automatically print out labels for samples based on the tests to be performed. Also, the second device will determine how best to deliver the test results to the receiving agency.

The second device collects information that may be entered at the device UI, may be entered through a web application running on the device, or may be extracted from the lab test prescription form as produced by the first device. Thus, the second MFD scans the lab test prescription form document producing an electronic image. This electronic image is analyzed to transform the machine readable information on the lab test prescription form (glyphs or bar codes) into a format more amenable to further processes, such as an extensible markup language (XML) document.

The second device collects formatting information on the best format in which to deliver the lab results back to the receiving agency. The information entered on the form may be sufficient to deliver the lab test results in simple cases such as a fax back, but complex data entry/formatting may require significant transformation. This formatting information may be obtained from the lab test prescription form if the lab test prescription form has the information encoded on it, from a database internal to the MFD (if the MFD is capable of storing instructions for delivery), or from an external database (the instructions for delivery can be stored in an external database that the MFD is able to access).

The second device also automatically collects the lab test results from the test equipment. This may be done in a number of ways. For example, on older equipment that does not have network connectivity, the data can be copied from the testing equipment into a computer, or data printouts from the device can be scanned. On new equipment, the data can be collected directly from the testing equipment through wired or wireless connections.

The second device formats the test results from the test equipment for delivery to the receiving office. This outputs the test results using the best delivery format for the receiving office. For example, the formatting information contained on the lab test prescription form may require processing the data so that it fits into a particular schema for a particular EMR. The second device then sends the data to the receiving office either through the phone or through the internet. If the information is to be faxed back, the data can be encoded in the fax stream. If the information is to be delivered over the internet, the lab test results are processed accordingly. Electronic transfer methods include transfer directly into the EMR database, by e-mail, as a document to a repository, or as an XML document. In addition, the lab test results can also be maintained for some period of time in a database from which they can be retrieved by the receiving office or other agency upon request.

The devices discussed herein do not require any infrastructure beyond what is available today. If the requesting office sends a paper lab test prescription form, as is currently common, the lab test prescription form can be scanned, the image stored and associated with information that was entered through the device UI, a paper UI or a web UI. When the second device sends lab test results to the receiving office, the device also sends data that will be treated as an ordinary fax by an ordinary fax machine, but will be treated as an encoded image or direct binary data packaged for immediate use by a device capable of retrieving the encoded binary data.

As mentioned above, the lab test results can be sent to a different doctor's office and/or returned to the originating doctor's office. For convenience, the device at this location is referred to herein as a "third" device (although it could be the first device, discussed above). The third device is able to receive information from the second device. It is also able to transform the data into an appropriate form, if the second device's formatting needs to be adjusted. The third device may transform the lab results into a form acceptable to the EMR, or it may store the document locally.

The third device has the capability to transform the document into either machine readable or human readable form. The third device has a processor that transforms the incoming lab information into a format acceptable to the office then outputting that data to the appropriate device. For example, if the office uses an EMR, the device would transform the information into a data format acceptable to the EMR and present that data to the EMR through an appropriate interface. If, on the other hand, the office uses a paper medical record, it may simply print the information. To perform this transformation, the third device stores the incoming lab test results (potentially from a fax transmission) in local storage. The third device locates the elements of the fax that contain the binary data and processes the binary data in accordance with instructions. These instructions may be stored either locally on the machine or in an external database. The processing will be appropriate to the lab test results being received. Processing may entail the retrieval of additional laboratory data from external databases. The lab test results also can be printed out.

Figure 1:
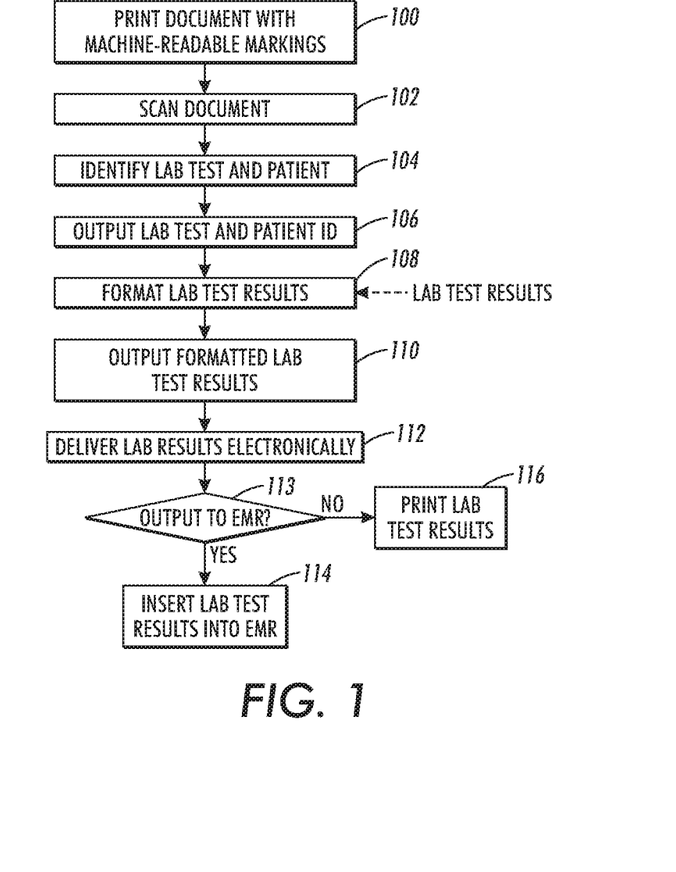
FIG. 1 is a flow diagram illustrating embodiments herein.

Referring now to the drawings, FIG. 1 illustrates an exemplary method embodiment in flowchart form. In the following description, for convenience a "first" document processing device is assumed to be located at the medical provider's office (e.g., doctor's office) that issues the lab test prescription and will receive the lab test results back, and the "second" document processing device is assumed to be located at the lab testing facility. The first document processing device and the second document processing device can be identical devices or different devices that can communicate with one another. Further, as would be understood by one ordinarily skilled in the art, many more similar document processing devices could be in communication with one another to facilitate exchange of the various lab test results relating to a given patient.

Figure 2:
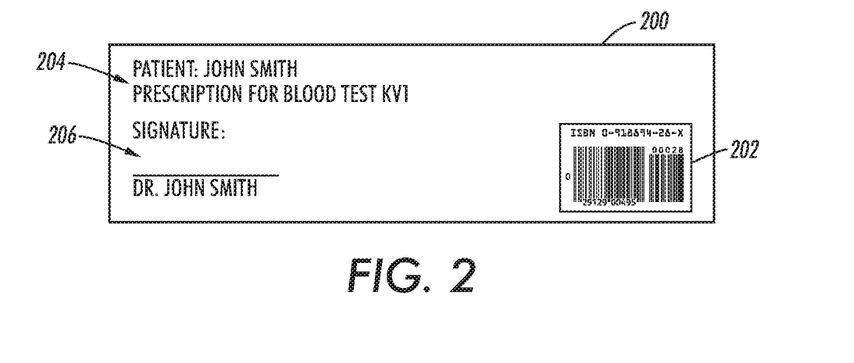
FIG. 2 is a schematic diagram of a document according to embodiments herein.

More specifically, in item 100, a first document processing device automatically prints machine-readable markings (and potentially-human readable markings) to create a document. FIG. 2 illustrates one exemplary document for a blood test. This document 200 has printed thereon one or more machine readable markings 202 (which can only be read by a machine and are not usually human-readable) as well as any necessary human readable markings (text and graphics) 204, 206. The machine readable markings 202 contain information that identifies the patient, information of at least one lab test to be performed on the identified patient, and formatting information appropriate for the first document processing device with respect to the desired format for the lab test results.

After being printed, the patient can carry this printed document 200 to the lab testing facility (and/or the document can be printed on the second document processing device at the lab testing facility). Thus, in item 102, the method scans the document the using a second document processing device to allow the second document processing device to identify the lab test to be performed on the patient based on the machine readable markings in item 104.

As shown in item 106, some embodiments herein can use the second document processing device to automatically output to a lab technician the identification of the patient and the identification of the lab test to be performed. A lab technician performs the appropriate lab tests on the patient using lab testing equipment, that is operatively connected to, or in communication with the second document processing device. After these lab tests have been performed on the patient, in item 108, the second document processing device automatically formats the lab test to be compatible with the needs of the first document processing device based on the formatting information that is contained within the machine readable markings.

These formatted lab test results are then automatically output from the second document processing device to the first document processing device in item 110. These can be output by transmitting the lab test results as a facsimile transmission from the second document processing device to the first document processing device. These lab results are delivered electronically to the receiving office (possibly also to the requesting office) in step 112. Once delivered, the first document processing device determines how best to process the data. If the data is to be inserted into an EMR 113, the electronic record that was delivered is formatted to meet the requirements of the EMR system 114. If the data is to be inserted into a paper medical record 113, it is printed 116. Alternatively, the second document device may be able to insert the data directly into the receiving offices EMR system, bypassing the first document processing device on the return trip.

Figure 3:
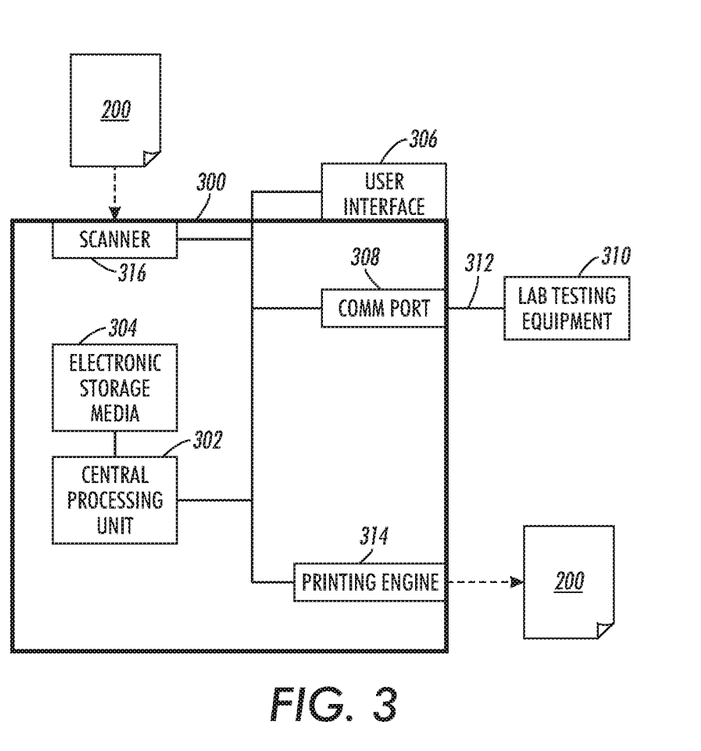
FIG. 3 is a schematic diagram of a document processing device according to embodiments herein.

A number of devices embodiments are presented in this disclosure. One of the standalone devices is shown in FIG. 3, as item 300. In this example, item 300 comprises a document processing device that has a processor 302 (central processing unit) that executes instructions stored on connected computer-readable storage media 304 to perform the various operations mentioned herein. Further, this device 300 includes a user interface 306 that can receive information from the patient or a medical provider, a printing engine 314 (operatively connected to the processor 302) that can print the document 200, and a scanner 316 (operatively connected to the processor 302) that can scan the document 200. The processor 302 automatically processes the scanned image to identify the lab test to be performed on the patient, based on the machine readable markings.

This device further includes a communications port 308 that is operatively connected to the processor 302. The communications port 308 is also operatively connected to the lab testing equipment 310 (through any form of local or wide area network 312) that is used to perform the lab test on the patient and can automatically receive the lab test results from such lab testing equipment. The processor 302 automatically formats the lab test results based on the formatting information from the machine readable markings, and the communications port 308 automatically outputs the formatted lab test results. Once again, the communications port 308 can output the lab test results as a facsimile or an electronic medical record (EMR).

Figure 4:
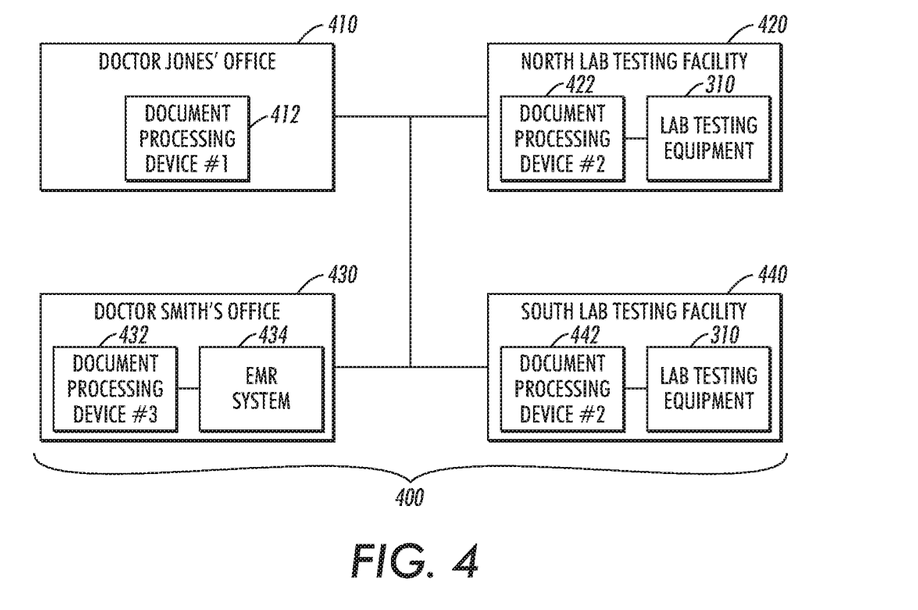
FIG. 4 is a schematic diagram of a system embodiment according to embodiments herein.

System embodiments are also disclosed herein. One system embodiment 400 that is shown in FIG. 4 includes a first document processing device 412 that is located in a first office (e.g. Dr. Jones' office 410) and a second document processing device 422 that is in communication with the first document processing device 412 and is located in a lab testing facility (e.g. North Lab Testing Facility 420). In addition, additional document processing devices 432, 442 can be similarly located in other doctor's offices 430 or other lab testing facilities 440.

Each of these devices 412, 422, includes, respectively, first and second processors operatively connected to first and second computer-readable storage media that are shown and discussed in greater detail above, with respect to FIG. 3. Again, the processors automatically execute instructions stored on the first and second computer-readable storage media. Such devices also include, respectively, first and second printing engines, first and second scanners, and first and second communication ports, and first and second user interfaces (each of which is operatively connected to their respective processors) as also discussed above.

Therefore, the first document processing device 412 prints the previously described document. Thus, the first printing engine prints the machine readable markings that contain information of the patient, information of the lab test(s) to be performed, and formatting information. The patient then generally carries the printed document to the lab testing facility 420 and presents the printed document to a lab technician, who then scans the document using the second document processing device 422. Thus, the second scanner produces a scanned image and the second processor automatically processes the scanned image to identify the lab test to be performed on the patient, based on the machine readable markings. The second document processing device 422 can then automatically print or display, for the lab technician, an identification of the patient and an identification of the lab test to be performed (using the second printing engine or the second user interface).

One feature of the embodiments herein is that the second communications port of the second document processing device 422 is operatively connected to the lab testing equipment 310 used to perform the lab tests on the patient and, therefore, automatically electronically receives the lab test results from the lab testing equipment 310. Another feature of the embodiments herein is that the second processor automatically formats the lab test results based on the formatting information from the machine readable markings to automatically convert the lab test results into a format that can be used by the first document processing device 412.

Then, after the lab test results are properly formatted for the first document processing device 412, the second document processing device 422 automatically outputs the formatted lab test results to the first document processing device 412. Once again, the communications port can output the lab test results as a facsimile or to an electronic medical record (EMR).

For example, if one of the document processing devices 422, 442 within the lab testing facilities 420, 440 were outputting lab test results to Dr. Smith's office 430 that utilizes an EMR system 434, the test results could be automatically output as an electronic medical record either directly to the EMR system 434 or indirectly to the EMR system through the third document processing device 432. In addition, the machine readable markings could identify multiple recipients of the lab test results and identify multiple different formats, if the different recipients needed the lab test results in different formats. The sophistication of the system embodiments herein can easily match the sophistication of any systems currently utilized by medical providers or laboratory facilities and can range from sending simple faxes to sending highly complex and controlled formatted lab test results to electronic medical record systems. Further, if the embodiments herein are utilized with EMR systems, before the document is printed, the device 432 can identify the patient using the EMR system and select the lab test to be performed using the EMR system when creating a lab test prescription.

Many computerized devices and printers are discussed above. Many forms of printing devices are currently available from manufactures such as Xerox Corporation, Norwalk, Conn., USA. Computerized devices that include chip-based central processing units (CPU's), input/output devices (including graphic user interfaces (GUI), memories, comparators, processors, etc. are well-known and readily available devices produced by manufactures such as International Business Machines Corporation, Armonk N.Y., USA and Apple Computer Co., Cupertino Calif., USA. Such computerized devices and printers commonly include input/output devices, power supplies, processors, electronic storage memories, wiring, etc., the details of which are omitted herefrom to allow the reader to focus on the salient aspects of the embodiments described herein. Similarly, scanners and other similar peripheral equipment are available from Xerox Corporation, Norwalk, Conn., USA and Visioneer, Inc. Pleasanton, Calif., USA and the details of such devices are not discussed herein for purposes of brevity and reader focus.

The words printer, printing device, output device, etc., as used herein encompasses any apparatus, such as a digital copier, bookmaking machine, facsimile machine, multi-function machine, etc. which performs a print outputting function for any purpose. The details of printers, printing engines, etc. are well-known by those ordinarily skilled in the art and are discussed in, for example, U.S. Pat. No. 6,032,004, the complete disclosure of which is fully incorporated herein by reference. The embodiments herein can encompass embodiments that print in color, monochrome, or handle color or monochrome image data. All foregoing embodiments are specifically applicable to electrostatographic and/or xerographic machines and/or processes.

When used herein the term automatic or automatically means that a system or method performs the action without requiring any further user input and occurs as the result of some action being completed or some state being achieved.

It will be appreciated that the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims. The claims can encompass embodiments in hardware, software, and/or a combination thereof. Unless specifically defined in a specific claim itself, steps or components of the invention should not be implied or imported from any above example as limitations to any particular order, number, position, size, shape, angle, color, or material.

What is claimed is:

1. A method comprising:
    scanning a document printed by a printer of a first document processing device using a scanner of a second document processing device, the document comprising machine readable encoded information, the machine readable encoded information comprising information of a patient, information of at least one lab test to be performed, and return delivery format information;
    identifying, using the second document processing device, the lab test to be performed on a patient by reading the lab test from the machine readable encoded information scanned during the scanning of the document;
    after the lab test has been performed on the patient using lab testing equipment operatively connected to the second document processing device to produce lab test results, formatting the lab test results in a format required by the first document processing device, using the second document processing device, by reading the return delivery format information from the machine readable encoded information scanned during the scanning of the document to produce formatted lab test results; and
    delivering the formatted lab test results from the second document processing device to the first document processing device.

2. The method according to claim 1, the delivering of the formatted lab test results comprising outputting a facsimile transmission from the second document processing device to the first document processing device.

3. The method according to claim 1, the delivering of the formatted lab test results comprising outputting an electronic medical record (EMR) from the second document processing device to the first document processing device.

4. The method according to claim 1, further comprising:
before the scanning of the document, identifying the patient using an electronic medical record (EMR) system operatively connected to the first document processing device; and
selecting the lab test to be performed using the EMR system.

5. The method according to claim 1, wherein the formatting of the lab test results produces the formatted lab test results to have a format of an electronic medical record (EMR) system operatively connected to the first document processing device.

6. The method according to claim 1, wherein the formatting of the lab test results produces multiple different formatted lab test results having multiple different formats corresponding to multiple recipients identified by the return delivery format information.

7. The method according to claim 1, the document further comprising human readable information.

8. A method comprising:
scanning a document printed by a printer of a first document processing device using a scanner of a second document processing device separate from the first document processing device, the document comprising machine readable encoded information, the machine readable encoded information comprising information of a patient, information of at least one lab test to be performed, and return delivery format information;
identifying, using the second document processing device, the lab test to be performed on a patient by reading the lab test from the machine readable encoded information scanned during the scanning of the document;
outputting to a lab technician, using the second document processing device, an identification of the patient and an identification of the lab test to be performed;
after the lab test has been performed on the patient using lab testing equipment operatively connected to the second document processing device to produce lab test results, formatting the lab test results in a format required by the first document processing device, using the second document processing device, by reading the return delivery format information from the machine readable encoded information scanned during the scanning of the document to produce formatted lab test results; and
delivering the formatted lab test results from the second document processing device to the first document processing device.

9. The method according to claim 8, the delivering of the formatted lab test results comprising outputting a facsimile transmission from the second document processing device to the first document processing device.

10. The method according to claim 8, the delivering of the formatted lab test results comprising outputting an electronic medical record (EMR) from the second document processing device to the first document processing device.

11. The method according to claim 8, further comprising:
before the scanning of the document, identifying the patient using an electronic medical record (EMR) system operatively connected to the first document processing device; and
selecting the lab test to be performed using the EMR system.

12. The method according to claim 8, wherein the formatting of the lab test results produces the formatted lab test results to have a format of an electronic medical record (EMR) system operatively connected to the first document processing device.

13. The method according to claim 8, wherein the formatting of the lab test results produces multiple different formatted lab test results having multiple different formats corresponding to multiple recipients identified by the return delivery format information.

14. The method according to claim 8, the document further comprising human readable information.

15. A system comprising:
a first document processing device in communication with a second document processing device,
wherein the first document processing device comprises a printer adapted to print machine readable encoded information on a document,
wherein the machine readable encoded information comprises information of a patient, information of at least one lab test to be performed, and return delivery format information,
wherein the second document processing device comprises a scanner adapted to scan the document printed by the first document processing device,
wherein the second document processing device is adapted to identify the lab test to be performed on a patient by reading the lab test from the machine readable encoded information scanned during scanning of the document,
wherein the second document processing device is adapted to format lab test results in a format required by the first document processing device by reading the return delivery format information from the machine readable encoded information scanned during the scanning of the document to produce formatted lab test results, after the lab test has been performed on the patient using lab testing equipment operatively connected to the second document processing device, and
wherein the second document processing device is adapted to deliver the formatted lab test results to the first document processing device.

16. The system according to claim 15, wherein the second document processing device is adapted to deliver the formatted lab test results to the first document processing device by outputting a facsimile transmission from the second document processing device to the first document processing device.

17. The system according to claim 15, wherein the second document processing device is adapted to deliver the formatted lab test results to the first document processing device by outputting an electronic medical record (EMR) from the second document processing device to the first document processing device.

18. The system according to claim 15, wherein the second document processing device is adapted to format the lab test results to have a format of an electronic medical record (EMR) system operatively connected to the first document processing device.

19. The system according to claim 15, wherein the second document processing device is adapted to format the lab test results to produce multiple different formatted lab test results having multiple different formats corresponding to multiple recipients identified by the return delivery format information.

20. The system according to claim 15, wherein the first document processing device is adapted to print human readable information on the document.

* * * * *